US008992895B2

(12) United States Patent
Halpern et al.

(10) Patent No.: US 8,992,895 B2
(45) Date of Patent: Mar. 31, 2015

(54) SUNSCREEN COMPOSITIONS

(71) Applicant: L'Oreal, Paris (FR)

(72) Inventors: Susan Halpern, Basking Ridge, NJ (US); Jean-Thierry Simonnet, Mamaroneck, NY (US); Anil Shah, East Windsor, NJ (US)

(73) Assignee: L'Oreal, Paris (FR)

( * ) Notice: Subject to any disclaimer, the term of this patent is extended or adjusted under 35 U.S.C. 154(b) by 176 days.

(21) Appl. No.: 13/719,474

(22) Filed: Dec. 19, 2012

(65) Prior Publication Data

US 2014/0170192 A1    Jun. 19, 2014

(51) Int. Cl.
| *A61K 8/00*  | (2006.01) |
| *A61K 8/18*  | (2006.01) |
| *A61Q 17/04* | (2006.01) |
| *A61K 8/02*  | (2006.01) |
| *A61K 8/90*  | (2006.01) |
| *A61K 8/86*  | (2006.01) |
| *A61K 8/81*  | (2006.01) |

(52) U.S. Cl.
CPC ... *A61K 8/90* (2013.01); *A61K 8/86* (2013.01); *A61K 8/8164* (2013.01); *A61Q 17/04* (2013.01)
USPC .......................................... 424/59; 424/401

(58) Field of Classification Search
None
See application file for complete search history.

(56) References Cited

U.S. PATENT DOCUMENTS

| 7,339,013    | B2  |   | 3/2008  | Pagnoux et al.      |         |
|--------------|-----|---|---------|---------------------|---------|
| 8,557,227    | B2  | * | 10/2013 | Simonnet et al.     | 424/59  |
| 2004/0028709 | A1  | * | 2/2004  | Dueva et al.        | 424/401 |
| 2004/0101498 | A1  | * | 5/2004  | Koshti et al.       | 424/59  |
| 2006/0110379 | A1  | * | 5/2006  | Green et al.        | 424/94.5|
| 2008/0305057 | A1  | * | 12/2008 | Fox                 | 424/60  |
| 2009/0035234 | A1  | * | 2/2009  | Cunningham et al.   | 424/59  |
| 2012/0014891 | A1  | * | 1/2012  | Rastrelli et al.    | 424/60  |
| 2013/0129650 | A1  | * | 5/2013  | Simonnet et al.     | 424/60  |

OTHER PUBLICATIONS

Notification of Transmittal of the International Search Report and the Written Opinion of the International Searching Authority, or the Declaration; International Search Report; Written Opinion of the International Searching Authority, International Application No. PCT/US2013/076417.
U.S. Appl. No. 13/304,195, Simonnet et al.
U.S. Appl. No. 13/304,202, Simonnet et al.
Hollow Sphere Technology, "An SPF Booster with excellent product feel for Sunscreens and Cosmetics," SunSpheres™, Rohm and Haas Company, 2004, 2 pages.

* cited by examiner

*Primary Examiner* — Carlos Azpuru
*Assistant Examiner* — Casey Hagopian
(74) *Attorney, Agent, or Firm* — Novak Druce Connolly Bove + Quigg LLP

(57) ABSTRACT

The instant disclosure relates to sunscreen compositions. The sunscreen compositions include (a) at least one UV filter (b) at least one booster, (c) at least one thermosensitive polymer, and (d) at least one wetting agent. Sunscreen compositions comprising components (a)-(d) exhibit a surprisingly high sun protection factor (SPF). The disclosure further relates to methods of using the sunscreen compositions for protecting keratinous substances such as skin and hair from UV radiation.

33 Claims, No Drawings

SUNSCREEN COMPOSITIONS

FIELD OF THE DISCLOSURE

The present disclosure relates to sunscreen compositions comprising a unique combination of components that provide for a high Sun Protection Factor (SPF), and to methods of using the compositions to protect keratinous substrates such as skin and hair from UV radiation.

BACKGROUND

The negative effects of exposure to ultraviolet ("UV") light are well-known. Prolonged exposure to sunlight causes damage such as sunburn to the skin and dries out hair making it brittle. When skin is exposed to UV light having a wavelength of from about 290 nm to about 400 nm, long term damage can lead to serious conditions such as skin cancer.

UV light also contributes to aging by causing free radicals to form in the skin. Free radicals include, for example, singlet oxygen, hydroxyl radical, the superoxide anion, nitric oxide and hydrogen radicals. Free radicals attack DNA, membrane lipids and proteins, generating carbon radicals. These in turn react with oxygen to produce a peroxyl radical that can attack adjacent fatty acids to generate new carbon radicals. This cascade leads to a chain reaction producing lipid peroxidation products. Damage to the cell membrane results in loss of cell permeability, increased intercellular ionic concentration, and decreased ability to excrete or detoxify waste products. The end result is a loss of skin elasticity and the appearance of wrinkles. This process is commonly referred to as photoaging.

Sunscreens can be used to protect against UV damage and delay the signs of aging. The degree of UV protection afforded by a sunscreen composition is directly related to the amount and type of UV filters contained therein. The higher the amount of UV filters, the greater the degree of UV protection. Nevertheless, it is desirable to achieve the best photo protection efficacy with the lowest amount of UV filters. The inventors of the instant disclosure discovered ways to attain SPFs that were not previously attainable with such low amounts of overall UV filters.

SUMMARY OF THE INVENTION

The present disclosure relates to sunscreen compositions that have low amounts of UV filters, have excellent Sun Protection Factors (SPF), and exhibit good skin feel and other aesthetic properties. Typically, high amounts of UV filters are needed in sunscreen compositions to attain a SPF. The inventors discovered, however, that a combination of at least one UV filter, at least one booster, at least one thermosensitive polymer, and at least one wetting agent exhibits a surprisingly effective SPF (in addition to other beneficial properties). This allows for sunscreen compositions to be formulated using lower overall amounts of UV filters that nonetheless exhibit excellent sun protective properties.

In one aspect, the instant disclosure is directed to a sunscreen composition comprising at least one UV filter; at least one booster; at least one thermosensitive polymer; and at least one wetting agent. The at least one UV filter may be in an amount of about 1 to about 50 wt. %, based on the total weight of the sunscreen composition. The at least one booster may be in an amount of about 0.1 to about 25 wt. %, based on the total weight of the sunscreen composition. The at least one thermosensitive polymer may be in an amount of about 0.1 to about 10 wt. %, based on the total weight of the sunscreen composition. The at least one wetting agent may be in an amount of about 0.01 to about 5 wt. %, based on the total weight of the sunscreen composition. Moreover, the at least on UV filters may be in an amount of about 20 wt. %, based on the total weight of the sunscreen composition. The at least one booster may be in an amount of about 3 wt. % based on the total weight of the sunscreen composition. The at least one t polymer may be in an amount of about 1.0 wt. %, based on the total weight of the sunscreen composition. The at least one wetting agent may be in an amount of about 0.25 wt. %, based on the total weight of the sunscreen composition.

The at least one booster can be any booster known in the art. For example, the at least one booster may be selected from the group consisting of styrene/acrylates copolymer (Sunspheres®), calcium aluminum borosilicate, sodium borosilicate particulates, calcium/sodium borosilicate hollow microspheres, and calcium/sodium borosilicate microspheres. In one embodiment, the booster is styrene/acrylates copolymer (Sunspheres®).

The at least one thermosensitive polymer and the at least one wetting agent may be any thermosensitive polymer and wetting agent known in the art. In one embodiment, the thermosensitive polymer is bis-methoxy PEG 13 PEG-438/PPG-110 SMDI copolymer (ExpertGel®). In another embodiment, the wetting agent is a dimethicone copolyol compound such as PEG-12 dimethicone, which is a dimethicone copolyol compound.

The at least one UV filter can be any UV filter known in the art. In particular, combinations of UV filters are useful in the compositions described herein. In one embodiment, the at least one UV filter is a combination of UV filters comprising comprising octocrylene, avobenzone, oxybenzone, octislate, and homosalate. For instance, this combination of UV filters may be used in the following ratios relative to avobenzone:
the ratio of octocrylene to avobenzone is 1.6:1.0 to 2.4:1.0;
the ratio of oxybenzone to avobenzone 1.0:1.0 to 1.6:1.0;
the ratio of octislate to avobenzone is 0.8:1.0 to 1.3:1.0; and
the ratio of homosalate to avobenzone is 2.8:1.0 to 4.3:1.

Furthermore, the ratio of each UV filter relative to avobenzone may be about: 2.0:1.0:1.3:1.1:3.6 (octocrylene:avobenzone:oxybenzone:octislate:homosalate).

In another embodiment, the at least one UV filter is a combination of UV filters comprising octocrylene, avobenzone, octisalate, and homosalate, and optionally oxybenzone. For instance, this combination of UV filters may be used in the following ratios relative to avobenzone:
the ratio of octocrylene to avobenzone is 1.6:1.0 to 2.4:1.0,
the ratio of oxybenzone to avobenzone 0.0:1.0 to 0.016:1.0,
the ratio of octislate to avobenzone is 1.3:1.0 to 2.0:1.0, and
the ratio of homosalate to avobenzone is 2.3:1.0 to 3.6:1.

Furthermore, the ratio of each UV filter relative to avobenzone may be about: 2.0:1.0:0.0:1.7:3.0 (octocrylene:avobenzone:oxybenzone:octislate:homosalate).

In another embodiment, the at least one UV filter is a combination of UV filters comprising octocrylene, butyl methoxydibenzoylmethane, bis-ethylhexyloxyphenol methoxyphenyl triazine, ethylhexyl triazone, terephthalylidene dicamphor sulfonic acid, and drometrizole trisiloxane. For instance, this combination of UV filters may be used in the following ratios relative to butyl methoxydibenzoylmethane:
the ratio of octocrylene to butyl methoxydibenzoylmethane is 0.8:1.0 to 1.5:1.0;
the ratio of bis-ethylhexyloxyphenol methoxyphenyl triazine to butyl methoxydibenzoylmethane 0.3:1.0 to 0.8:1.0;

the ratio of ethylhexyl triazone to butyl methoxydibenzoylmethane is 0.3:1.0 to 1.0:1.0;

the ratio of terephthalylidene dicamphor sulfonic acid to butyl methoxydibenzoylmethane is 0.1:1.0 to 0.5:1.0; and the ratio of drometrizole trisiloxane to butyl methoxydibenzoylmethane is 0.3:1.0 to 1.0:1.0.

Furthermore, the ratio of each UV filter relative to butyl methoxydibenzoylmethane may be about: 1.2:1.0:0.5:0.6:0.4:0.6 (octocrylene:butyl methoxydibenzoylmethane:bis-ethylhexyloxyphenol methoxyphenyl triazine:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, ethylhexyl triazone, terephthalylidene dicamphor sulfonic acid, and drometrizole trisiloxane. For instance, this combination of UV filters may be used in the following ratios relative to butyl methoxydibenzoylmethane:

the ratio of octocrylene to butyl methoxydibenzoylmethane is 0.6:1.0 to 1.25:1.0;

the ratio of ethylhexyl triazone to butyl methoxydibenzoylmethane is 0.4:1.0 to 1.0:1.0;

the ratio of terephthalylidene dicamphor sulfonic acid to butyl methoxydibenzoylmethane is 0.3:1.0 to 0.7:1.0; and the ratio of drometrizole trisiloxane to butyl methoxydibenzoylmethane is 0.4:1.0 to 1.1:1.0.

Furthermore, the ratio of each UV filter relative to butyl methoxydibenzoylmethane may be about: 1.0:1.0:0.7:0.5:0.7 (octocrylene:butyl methoxydibenzoylmethane:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane. For instance, this combination of UV filters may be used in the following ratios relative to butyl methoxydibenzoylmethane:

the ratio of octocrylene to butyl methoxydibenzoylmethane is 0.8:1.0 to 1.2:1.0;

the ratio of bis-ethylhexyloxyphenol methoxyphenyl triazine to butyl methoxydibenzoylmethane is 0.2:1.0 to 0.6:1.0;

the ratio of terephthalylidene dicamphor sulfonic acid to butyl methoxydibenzoylmethane is 0.0.25:1.0 to 0.75:1.0; and the ratio of drometrizole trisiloxane to butyl methoxydibenzoylmethane is 0.4:1.0 to 0.8:1.0. [Synergistic combination from PR2012572]

Furthermore, the ratio of each UV filter relative to butyl methoxydibenzoylmethane may be about: 1.0:1.0:0.4:0.4:0.6 (octocrylene:butyl methoxydibenzoylmethane:bis-ethylhexyloxyphenol methoxyphenyl triazine:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane. For instance, this combination of UV filters may be used in the following ratios relative to butyl methoxydibenzoylmethane is as follows:

the ratio of octocrylene to butyl methoxydibenzoylmethane is 0.8:1.0 to 1.3:1.0;

the ratio of bis-ethylhexyloxyphenol methoxyphenyl triazine to butyl methoxydibenzoylmethane is 0.1:1.0 to 0.6:1.0;

the ratio of ethylhexyl triazone to butyl methoxydibenzoylmethane is 0.2:1.0 to 0.6:1.0; and the ratio of drometrizole trisiloxane to butyl methoxydibenzoylmethane is 0.3:1.0 to 0.7:1.0. [Synergistic combination from PR2012573]

Furthermore, the ratio of each UV filter relative to butyl methoxydibenzoylmethane may be about: 1.0:1.0:0.3:0.5:0.5 (octocrylene:butyl methoxydibenzoylmethane:bis-ethylhexyloxyphenol methoxyphenyl triazine:ethylhexyl triazone:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and terephthalylidene dicampohor sulfonic acid. For instance, this combination of UV filters may be used in the following ratios relative to butyl methoxydibenzoylmethane is as follows:

the ratio of octocrylene to butyl methoxydibenzoylmethane is 0.8:1.0 to 1.6:1.0;

the ratio of bis-ethylhexyloxyphenol methoxyphenyl triazine to butyl methoxydibenzoylmethane is 0.2:1.0 to 0.6:1.0;

the ratio of ethylhexyl triazone to butyl methoxydibenzoylmethane is 0.3:1.0 to 0.6:1.0; and the ratio of terephthalylidene dicampohor sulfonic acid to butyl methoxydibenzoylmethane is 0.01:1.0 to 0.3:1.0. [Synergistic combination from PR2012574]

Furthermore, the ratio of each UV filter relative to butyl methoxydibenzoylmethane may be about: 1.2:1.0:0.3:0.5:0.1 (octocrylene:butyl methoxydibenzoylmethane:bis-ethylhexyloxyphenol methoxyphenyl triazine:ethylhexyl triazone:terephthalylidene dicampohor sulfonic acid).

The present disclosure is also directed to methods of protecting a keratinous substrate from ultraviolet radiation and to methods of absorbing ultraviolet light. Such methods encompass applying a sunscreen composition to a keratinous substrate and subjecting the keratinous substrate to ultraviolet radiation.

DETAILED DESCRIPTION

Where the following terms are used in this specification, they are used as defined below.

The terms "comprising," "having," and "including" are used in their open, non-limiting sense.

The terms "a" and "the" are understood to encompass the plural as well as the singular.

As used herein, the expression "at least one" means one or more and thus includes individual components as well as mixtures/combinations.

"Cosmetically acceptable" means that the item in question is compatible with any keratinous substrate. For example, "cosmetically acceptable carrier" means a carrier that is compatible with any keratinous substrate.

A "physiologically acceptable medium" means a medium which is not toxic and can be applied to the skin, lips, hair, scalp, lashes, brows, nails or any other cutaneous region of the body. The composition of the instant disclosure may especially constitute a cosmetic or dermatological composition.

The phrase "essentially without" refers to less than or equal to 0.5, 0.1, 0.05 or 0.01 wt. %.

The phrase "stable emulsion" refers to a composition that does not undergo phase separation up to a temperature of 45 C.°.

The instant disclosure is directed to a sunscreen composition comprising at least one UV filter; at least one booster; at least one thermosensitive polymer; and at least one wetting agent.

The at least one UV filter may be in an amount of about 1, 2, 3, 4, 5, 6, 7, 8, 9, or 10 to about 15, 20, 25, 30, 35, 40, 45, or 50 wt. %, based on the total weight of the sunscreen composition. In other embodiments, the at least one UV filter may be present in a positive amount but not in excess of (no more than) about 5, 6, 7, 8, 9, 10, 11, 12, 13, 14, 15, 16, 17, 18, 19, 20, 21, 22, 23, 24, 25, 26, 27, 28, 29, or 30 wt. %, based on the total weight of the sunscreen composition. In one embodiment, the total amount of the at least one UV filter is about 20 wt. %, based on the total weight of the sunscreen composition.

The at least one booster may be in an amount of about 0.1, 0.5, 1, 1.5, or 2 to about 5, 10, 15, 20, or 25 wt. %, based on the total weight of the sunscreen composition. In one embodiment, the amount of booster is in an amount of about 3 wt. %, based on the total weight of the sunscreen composition.

The at least one thermosensitive polymer may be in an amount of about 0.1, 0.2, 0.3, 0.4, 0.5, 0.6, 0.7, 0.8 or 0.9 to about 2, 5, 6, 7, 8, 9, or 10 wt. %, based on the total weight of the sunscreen composition. In one embodiment, the at least one thermosensitive polymer is in an amount of about 1 wt. %, based on the total weight of the sunscreen composition.

The at least one wetting agent may be in an amount of about 0.01, 0.05, 0.1 or 0.15 to about 2, 3, 4, or 5 wt. %, based on the total weight of the sunscreen composition. In one embodiment, the at least one wetting agent is in an amount of about 0.25 wt. %, based on the total weight of the sunscreen composition.

The term "booster" or "SPF booster" means a compound or composition that when used in a formulation in conjunction with a UV filtering agent, increases the SPF of the formulation without increasing the amount of UV filtering agent in the formulation. The at least one booster can be any booster known in the art. For example, the at least one booster may be selected from the group consisting of styrene/acrylates copolymer (Sunspheres®), calcium aluminum borosilicate, sodium borosilicate particulates, calcium/sodium borosilicate hollow microspheres, and calcium/sodium borosilicate microspheres. In one embodiment, the booster is styrene/acrylates copolymer (Sunspheres®).

Other examples of boosters are those capable of reflecting UV light such as glass microspheres. Typically, the glass microspheres used in the compositions are essentially homogeneous and essentially uniform in sphericity and have a mean particle size of between about 5 µm and 70 µm, such as from about 10 µm to 20 µm. Glass microspheres useful in the present invention include hollow microspheres of calcium aluminum borosilicate (commercially available from Presperse Inc. under the trade name LUXSIL®), sodium borosilicate particulates (commercially available from PQ Corporation under the trade name Q-CEL 570), calcium/sodium borosilicate hollow microspheres (commercially available from 3M under the trade names ES 22 and 1 K), calcium/sodium borosilicate microspheres (commercially available from 3M's under the trade name Scotchlite™ $K_{20}$ product).

The compositions may include one or more boosters. The booster itself is not typically an active ingredient (i.e., UV filter), but is designed to enhance the effectiveness of the sunscreen actives present in the formulation. Suitable boosters include, but are not limited to, styrene/acrylates copolymer, sodium bentonites, highly purified white sodium bentonites, montmorillonite, fluorene derivatives, ester derivatives of cyano(9H-fluoren-9-ylidene), amides, malates, bis-urethanes, or any combinations thereof.

The at least one thermosensitive polymer and the at least one wetting agent may be any thermosensitive polymer and wetting agent known in the art. In one embodiment, the thermosensitive polymer is bis-methoxy PEG 13 PEG-438/PPG-110 SMDI copolymer (ExpertGel®). In another embodiment, the wetting agent is a dimethicone copolyol compound such as PEG-12 dimethicone, which is a demithicone copolyol compound.

The at least one UV filter can be any UV filter known in the art. In particular, combinations of UV filters are useful in the compositions described herein.

In one embodiment, the at least one UV filter is a combination of UV filters comprising octocrylene, avobenzone, oxybenzone, octisalate, and homosalate, as described in application Ser. No. 13/304,195, which is incorporated herein by reference in its entirety. For instance, this combination of UV filters may be used in the following ratios relative to avobenzone:
the ratio of octocrylene to avobenzone is 1.6:1.0 to 2.4:1.0;
the ratio of oxybenzone to avobenzone 1.0:1.0 to 1.6:1.0;
the ratio of octisalate to avobenzone is 0.8:1.0 to 1.3:1.0; and
the ratio of homosalate to avobenzone is 2.8:1.0 to 4.3:1.

Furthermore, the ratio of each UV filter relative to avobenzone may be about: 2.0:1.0:1.3:1.1:3.6 (octocrylene:avobenzone:oxybenzone:octisalate:homosalate).

In another embodiment, the at least one UV filter is a combination of UV filters comprising octocrylene, avobenzone, octisalate, and homosalate, and optionally oxybenzone, as described in application Ser. No. 13/304,202, which is incorporated herein by reference in its entirety. For instance, this combination of UV filters may be used in the following ratios relative to avobenzone:
the ratio of octocrylene to avobenzone is 1.6:1.0 to 2.4:1.0,
the ratio of oxybenzone to avobenzone 0.0:1.0 to 0.016:1.0,
the ratio of octisalate to avobenzone is 1.3:1.0 to 2.0:1.0, and
the ratio of homosalate to avobenzone is 2.3:1.0 to 3.6:1.

Furthermore, the ratio of each UV filter relative to avobenzone may be about: 2.0:1.0:0.0:1.7:3.0 (octocrylene:avobenzone:oxybenzone:octisalate:homosalate).

In another embodiment, the at least one UV filter is a combination of UV filters comprising octocrylene, butyl methoxydibenzoylmethane, bis-ethylhexyloxyphenol methoxyphenyl triazine, ethylhexyl triazone, terephthalylidene dicamphor sulfonic acid, and drometrizole trisiloxane, as described in application Ser. No. 13/719,328, which is incorporated herein by reference in its entirety. For instance, this combination of UV filters may be used in the following ratios relative to butyl methoxydibenzoylmethane:
the ratio of octocrylene to butyl methoxydibenzoylmethane is 0.8:1.0 to 1.5:1.0;
the ratio of bis-ethylhexyloxyphenol methoxyphenyl triazine to butyl methoxydibenzoylmethane 0.3:1.0 to 0.8:1.0;
the ratio of ethylhexyl triazone to butyl methoxydibenzoylmethane is 0.3:1.0 to 1.0:1.0;
the ratio of terephthalylidene dicamphor sulfonic acid to butyl methoxydibenzoylmethane is 0.1:1.0 to 0.5:1.0; and
the ratio of drometrizole trisiloxane to butyl methoxydibenzoylmethane is 0.3:1.0 to 1.0:1.0.

Furthermore, the ratio of each UV filter relative to butyl methoxydibenzoylmethane may be about: 1.2:1.0:0.5:0.6:0.4:0.6 (octocrylene:butyl methoxydibenzoylmethane:bis-ethylhexyloxyphenol methoxyphenyl triazine:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, ethylhexyl triazone, terephthalylidene dicamphor sulfonic acid, and drometrizole trisiloxane, as described in application Ser. No. 13/719,351, which is incorporated herein by reference in its entirety. For instance, this combination of UV filters may be used in the following ratios relative to butyl methoxydibenzoylmethane:

the ratio of octocrylene to butyl methoxydibenzoylmethane is 0.6:1.0 to 1.25:1.0;
the ratio of ethylhexyl triazone to butyl methoxydibenzoylmethane is 0.4:1.0 to 1.0:1.0;
the ratio of terephthalylidene dicamphor sulfonic acid to butyl methoxydibenzoylmethane is 0.3:1.0 to 0.7:1.0; and
the ratio of drometrizole trisiloxane to butyl methoxydibenzoylmethane is 0.4:1.0 to 1.1:1.0.

Furthermore, the ratio of each UV filter relative to butyl methoxydibenzoylmethane may be about: 1.0:1.0:0.7:0.5:0.7 (octocrylene:butyl methoxydibenzoylmethane:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,368, which is incorporated herein by reference in its entirety. For instance, this combination of UV filters may be used in the following ratios relative to butyl methoxydibenzoylmethane:

the ratio of octocrylene to butyl methoxydibenzoylmethane is 0.8:1.0 to 1.2:1.0;
the ratio of bis-ethylhexyloxyphenol methoxyphenyl triazine to butyl methoxydibenzoylmethane is 0.2:1.0 to 0.6:1.0;
the ratio of terephthalylidene dicamphor sulfonic acid to butyl methoxydibenzoylmethane is 0.0.25:1.0 to 0.75:1.0; and
the ratio of drometrizole trisiloxane to butyl methoxydibenzoylmethane is 0.4:1.0 to 0.8:1.0. [Synergistic combination from PR2012572]

Furthermore, the ratio of each UV filter relative to butyl methoxydibenzoylmethane may be about: 1.0:1.0:0.4:0.4:0.6 (octocrylene:butyl methoxydibenzoylmethane:bis-ethylhexyloxyphenol methoxyphenyl triazine:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,374, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.3:1.0;
the ratio of bis-ethylhexyloxyphenol methoxyphenyl triazine to butyl methoxydibenzoylmethane is 0.1:1.0 to 0.6:1.0;
the ratio of ethylhexyl triazone to butyl methoxydibenzoylmethane is 0.2:1.0 to 0.6:1.0; and
the ratio of drometrizole trisiloxane to butyl methoxydibenzoylmethane is 0.3:1.0 to 0.7:1.0. [Synergistic combination from PR2012573]

Furthermore, the ratio of each UV filter relative to butyl methoxydibenzoylmethane may be about: 1.0:1.0:0.3:0.5:0.5 (octocrylene:butyl methoxydibenzoylmethane:bis-ethylhexyloxyphenol methoxyphenyl triazine:ethylhexyl triazone:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and terephthalylidene dicampohor sulfonic acid, as described in application Ser. No. 13/719,393, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.6:1.0;
the ratio of bis-ethylhexyloxyphenol methoxyphenyl triazine to butyl methoxydibenzoylmethane is 0.2:1.0 to 0.6:1.0;
the ratio of ethylhexyl triazone to butyl methoxydibenzoylmethane is 0.3:1.0 to 0.6:1.0; and
the ratio of terephthalylidene dicampohor sulfonic acid to butyl methoxydibenzoylmethane is 0.01:1.0 to 0.3:1.0.

Furthermore, the ratio of each UV filter relative to butyl methoxydibenzoylmethane may be about: 1.2:1.0:0.3:0.5:0.1 (octocrylene:butyl methoxydibenzoylmethane:bis-ethylhexyloxyphenol methoxyphenyl triazine:ethylhexyl triazone:terephthalylidene dicampohor sulfonic acid).

The present disclosure is also directed to methods of protecting a keratinous substrate from ultraviolet radiation and to methods of absorbing ultraviolet light. Such methods encompass applying a sunscreen composition to a keratinous substrate and subjecting the keratinous substrate to ultraviolet radiation.

Gelling Agents

Examples of suitable hydrophilic gelling agents that may be used in the instant compostions include carboxyvinyl polymers such as the Carbopol products (carbomers) and the Pemulen products (acrylate/C10-C30-alkylacrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, which are optionally crosslinked and/or neutralized, for instance the poly(2-acrylamido-2-methylpropanesulfonic acid) sold by the company Hoechst under the trade name "Hostacerin AMPS" (CTFA name: ammonium polyacryldimethyltauramide); cellulose-based derivatives such as hydroxyethylcellulose; polysaccharides and especially gums such as xanthan gum; and mixtures thereof.

Lipophilic gelling agents (thickeners) that may be mentioned include modified clays such as hectorite and its derivatives, for instance the products sold under the name bentone.

In some instances, the gelling agent is ammonium acryloyldimethyltaurate/steareth-25 methacrylate crosspolymer, commercially available from Clariant under the tradename Aristoflex HMS.

Bis-Methoxy PEG-13 PEG-438/PPG-110 SMDI copolymer is a copolymer of PEG-438/PPG-110 and saturated methylene diphenyldiisocyanate (SMDI) monomers, endcapped with methoxy PEG-13.

The above lists are only examples and not limiting.

The gelling agent is typically used in an amount of about 0.05 to about 1.5% by weight, from about 0.08 to about 1.0% by weight, or about 0.1 to about 0.5% by weight, based on the total weight of the composition.

Wetting Agents

Examples of wetting agents that may be used in the instant compositions included dimethicone copolyol compounds such as PEG-12 dimethicone available from Dow Corning®.

Oils/Emollients

Examples of oils/emollients that may be included in the sunscreen compositions include: hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and caprylyl glycol; synthetic esters and ethers, especially of fatty acids, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew SL 205 by the company Ajinomoto; linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam oil, or the mixture of n-undecane ($C_{11}$) and of n-tridecane ($C_{13}$) sold under the reference Cetiol UT by the company Cognis; fluoro oils that are partially hydrocarbon-based and/or silicone-based, for instance those described in document JP-A-2 295 912; silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes; mixtures thereof.

Additional examples include benzoic acid esters of $C_9$-$C_{15}$ alcohols, isononyl iso-nonanoate, $C_{12}$-$C_{15}$ alkyl benzoate, or any combinations thereof.

Specific examples of oils/emollients include cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of $C_9$-$C_{15}$ alcohols, isononyl iso-nonanoate, alkanes, mineral oil, silicone, dimethyl polysiloxane, ether, polyoxypropylene butyl ether, polyoxypropylene cetyl ether, $C_{12}$-$C_{15}$ alkyl benzoate, aryl alkyl benzoate, Isopropyl Lauroyl sarcosinate, and any combinations thereof.

Examples of hydrophilic organic solvents that may be included in the sunscreen compositions include:
monohydric $C_1$-$C_8$ alcohols such as ethanol, propanol, butanol, isopropanol, isobutanol;
Polyethylene glycols from 6 to 80 ethylene oxides such as propylene glycol, isoprene glycol, butylene glycol, glycerol, sorbitol;
mono or di-alkyl isosorbides such as dimethyl isosorbide;
Examples of amphiphilic organic solvents include: polypropylene glycol (PPG) like propylene glycol alkyl ester or alkyl ether of PPG like PPG-23 oleyl ether and PPG-36 oleate.

The above lists are only examples and not limiting.

The total amount of oils/emollient present in the compositions is typically about 0.1, 0.5, 1.0, or 2.5 wt. % to about 5.0, 7.5, 10.0, 15.0, 20.0, or 30 wt. % of the total weight of the composition.

Film Formers

Film-formers are often incorporated into sunscreen compositions to ensure even coverage of the UV filters and can be used to render the composition water resistant. The film former is typically a hydrophobic material that imparts film forming and/or waterproofing characteristics. One such agent is polyethylene, which is available from New Phase Technologies as Performalene® 400, a polyethylene having a molecular weight of 400. Another suitable film former is polyethylene 2000 (molecular weight of 2000), which is available from New Phase Technologies as Performalene®. Yet, another suitable film former is synthetic wax, also available from New Phase Technologies as Performa® V-825. Other typical film-formers include acrylates/acrylamide copolymer, acrylates copolymer, acrylates/$C_{12}$-$C_{22}$ alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, Brassica Campestris/Aleuritis Fordi Oil copolymer, decamethyl cyclopentasiloxane (and) trimethylsiloxysilicate, and mixtures thereof. In some cases, the film former is acrylates/$C_{12}$-$C_{22}$ alkylmethacrylate copolymer sold under the tradename Allianz OPT® by ISP.

Many of the common film-forming polymers included in sunscreen compositions are not soluble in ethanol (such as PVP/Eicosene copolymer). A common film-former employed in ethanol based sunscreen products is Dermacryl LT or Dermacryl 79 marketed by Akzo Nobel (INCI Name: acrylates/octylacrylamide copolymer). Dermacryl LT (CAS Number: 80570-62-3) is a hydrophobic, high molecular weight carboxylated acrylic copolymer. It functions as a film-former in a broad range of cosmetic formulations, imparting waterproofing, increased occlusivity and decreased rub-off of actives.

The above lists are only examples and not limiting.

The total amount of film-formers present in the compositions is typically in an amount of about 0.1, 0.5, 1.0, or 5 wt. % to about 5, 10, 20, or 25 wt. %, based on the total weight of the composition.

Emulsifiers

The sunscreen compositions typically include at least one emulsifier such as an amphoteric, anionic, cationic or nonionic emulsifier, used alone or as a mixture, and optionally a co-emulsifier. The emulsifiers are chosen in an appropriate manner according to the emulsion to be obtained (W/O or O/W). The emulsifier and the co-emulsifier are generally present in the composition in a proportion ranging from 0.3 wt. % to 30 wt. % and preferably from 0.5 wt. % to 20 wt. % by relative to the total weight of the composition.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt. A crosslinked elastomeric solid organopolysiloxane comprising at least one oxyalkylene group, such as those obtained according to the procedure of Examples 3, 4 and 8 of U.S. Pat. No. 5,412,004 and of the examples of U.S. Pat. No. 5,811,487, especially the product of Example 3 (synthesis example) of U.S. Pat. No. 5,412,004, such as the product sold under the reference KSG 21 by the company Shin-Etsu, may also be used as surfactants for W/0 emulsions.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The fatty acid esters of a sugar that can be used as nonionic amphiphilic lipids can be chosen in particular from the group comprising esters or mixtures of esters of a $C_8$-$C_{22}$ fatty acid and of sucrose, of maltose, of glucose or of fructose, and esters or mixtures of esters of a $C_{14}$-$C_{22}$ fatty acid and of methylglucose.

The $C_8$-$C_{22}$ or $C_{14}$-$C_{22}$ fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearte, sucrose distearate, sucrose tristearate and mixtures thereof, such as the products sold by the company Croda under the name Crodesta F50, F70, F110 and F160 having, respectively, an HLB (Hydrophilic Lipophilic Balance) of 5, 7, 11 and 16; and, by way of example of esters or of mixtures of esters of a fatty acid and of methylglucose, mention may be made of the disearate of methylglucose and of polyglycerol-3, sold by the company Goldschmidt under the name Tego-care 450. Mention may also be made of glucose monoesters or maltose monoesters, such as methyl O-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a $C_8$-$C_{22}$ fatty alcohol and of glucose, of maltose, of sucrose or of fructose, and ethers or mixtures of ethers of a $C_{14}$-$C_{22}$ fatty alcohol and of methylglucose. They are in particular alkylpolyglucosides.

The $C_8$-$C_{22}$ or $C_{14}$-$C_{22}$ fatty alcohols forming the fatty unit of the ethers that can be used in the emulsion of the present disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglucoside and laurylglucoside sold, for example, by the company Henkel under the respective names Plantaren 2000 and Plantaren 1200, cetostearylglucoside, optionally as a mixture with cetostearyl alcohol, sold, for example, under the name Montanov 68 by the company Seppic, under the name Tegocare CG90 by the company Goldschmidt and under the name Emulgade KE3302 by the company Henkel, and also arachidylglucoside, for example in the form of the mixture of arachidyl and behenyl alcohols and of arachidylglucoside sold under the name Montanov 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The glycerol fatty esters that can be used as nonionic amphiphilic lipids can be chosen in particular from the group comprising the esters formed from at least one acid comprising a saturated linear alkyl chain having from 16 to 22 carbon atoms, and from 1 to 10 glycerol units. Use may be made of one or more of these glycerol fatty esters in the emulsion of the instant disclosure.

These esters may be chosen in particular from stearates, behenates, arachidates, palmitates and mixtures thereof. Stearates and palmitates are preferably used.

By way of example of a surfactant that can be used in the emulsion of the instant disclosure, mention may be made of decaglycerol monostearate, distearate, tristearate and pentastearate (10 glycerol units) (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1-S, 2-S, 3-S and 5-S by the company Nikko, and diglyceryl monostearate (CTFA name: polyglyceryl-2 stearate) such as the product sold by the company Nikko under the name Nikkol DGMS.

The sorbitan fatty esters that can be used as nonionic amphiphilic lipids chosen in particular from the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid comprising at least one saturated linear alkyl chain, having, respectively, from 16 to 22 carbon atoms, and from sorbitol or from ethoxylated sorbitol. The oxyethylenated esters generally comprise from 1 to 100 ethylene oxide units, and preferably from 2 to 40 ethylene oxide (EO) units.

These esters can be chosen in particular from stearates, behenates, arachidates, palmitates and mixtures thereof. Stearates and palmitates are preferably used.

By way of example of sorbitan fatty ester and of an oxyethylenated sorbitan fatty ester, mention may be made of sorbitan monostearate (CTFA name: sorbitan stearate) sold by the company ICI under the name Span 60, sorbitan monopalmitate (CTFA name: sorbitan palmitate) sold by the company ICI under the name Span 40, or sorbitan 20 EO tristearate (CTFA name: polysorbate 65) sold by the company ICI under the name Tween 65.

The ethoxylated fatty ethers are typically ethers made up of 1 to 100 ethylene oxide units and of at least one fatty alcohol chain having from 16 to 22 carbon atoms. The fatty chain of the ethers can be chosen in particular from behenyl, arachidyl, stearyl and cetyl units, and mixtures thereof, such as cetearyl.

By way of example of ethoxylated fatty ethers, mention may be made of ethers of behenyl alcohol comprising 5, 10, 20 and 30 ethylene oxide units (CTFA names: beheneth-5, beheneth-10, beheneth-20 and beheneth-30), such as the products sold under the names Nikkol BBS, BB10, BB20 and BB30 by the company Nikko, and the ether of stearyl alcohol comprising 2 ethylene oxide units (CTFA name: steareth-2), such as the product sold under the name Brij 72 by the company ICI.

The ethoxylated fatty esters that can be used as nonionic amphiphilic lipids are esters made up of 1 to 100 ethylene oxide units and of at least one fatty acid chain comprising from 16 to 22 carbon atoms. The fatty chain of the esters can be chosen in particular from stearate, behenate, arachidate and palmitate units, and mixtures thereof. By way of example of ethoxylated fatty esters, mention may be made of the ester of stearic acid comprising 40 ethylene oxide units, such as the product sold under the name Myrj 52 (CTFA name: PEG-40 stearate) by the company ICI, and the ester of behenic acid comprising 8 ethylene oxide units (CTFA name: PEG-8 behenate), such as the product sold under the name Compritol HD5 ATO by the company Gattefosse.

The block copolymers of ethylene oxide and of propylene oxide that can be used as nonionic amphiphilic can be chosen in particular from poloxamers and in particular from Poloxamer 231, such as the product sold by the company ICI under the name Pluronic L81 of formula (V) with x=z=6, y=39 (HLB 2); Poloxamer 282, such as the product sold by the company ICI under the name Pluronic L92 of formula (V) with x=z=10, y=47 (HLB 6); and Poloxamer 124, such as the product sold by the company ICI under the name Pluronic L44 of formula (V) with x=z=11, y=21 (HLB 16).

As nonionic amphiphilic lipids, mention may also be made of the mixtures of nonionic surfactants described in document EP-A-705593, incorporated herein for reference.

Suitable hydrophobically-modified emulsifiers include, for example, inulin lauryl carbamate, commercially available from Beneo Orafti under the tradename Inutec SP1.

The above lists are only examples and not limiting.

The total amount of emulsifier present in the compositions is typically in an amount of about 0.1, 0.2, or 0.5 wt. % to about 4.0, 5.0, 6.0, or 7.5 wt. %, based on the total weight of the composition.

Additional Sunscreen Filters (Protective Agents)

The sunscreen compositions can include additional sunscreen filters such as, for example, mineral UV filters. Examples of mineral UV filters include pigments and nanopigments (mean size of the primary particles is generally is from 5 nm to 100 nm or from 10 nm to 50 nm) of treated or untreated metal oxides such as, for example, nanopigments of titanium oxide (amorphous or crystallized in rutile and/or anatase form), of iron oxide, of zinc oxide, of zirconium oxide or of cerium oxide. The treated nanopigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal (titanium or aluminium) alkoxides, polyethylene, silicones, proteins (collagen or elastin), alkanolamines, silicon oxides, metal oxides, sodium hexametaphosphate, alumina or glycerol. The treated nanopigments may more particularly be titanium oxides treated with:

silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide;

alumina and aluminium stearate, such as the product "Microtitanium Dioxide MT 100 T" from the company Tayca;

alumina and aluminium laurate, such as the product "Microtitanium Dioxide MT 100 S" from the company Tayca;

iron oxides and iron stearate, such as the product "Microtitanium Dioxide MT 100 F" from the company Tayca;

silica, alumina and silicone, such as the products "Microtitanium Dioxide MT 100 SAS", "Microtitanium Dioxide MT 600 SAS" and "Microtitanium Dioxide MT 500 SAS" from the company Tayca;

sodium hexametaphosphate, such as the product "Microtitanium Dioxide MT 150 W" from the company Tayca;

octyltrimethoxysilane, such as the product "T-805" from the company Degussa;

alumina and stearic acid, such as the product "UVT-M160" from the company Kemira;

alumina and glycerol, such as the product "UVT-M212" from the company Kemira;

alumina and silicone, such as the product "UVT-M262" from the company Kemira.

Other titanium oxide nanopigments treated with a silicone are $TiO_2$ treated with octyltrimethylsilane and for which the mean size of the elementary particles is between 25 and 40 nm, such as the product sold under the trade name "T805" by the company Degussa Silices, $TiO_2$ treated with a polydimethylsiloxane and for which the mean size of the elementary particles is 21 nm, such as the product sold under the trade name "70250 Cardre UF TiO2SI3" by the company Cardre, anatase/rutile $TiO_2$ treated with a polydimethylhydrogenosiloxane and for which the mean size of the elementary particles is 25 nm, such as the product sold under the trade name "Microtitanium Dioxide USP Grade Hydrophobic" by the company Color Techniques.

Uncoated titanium oxide nanopigments are sold, for example, by the company Tayca under the trade names "Microtitanium Dioxide MT 500 B" or "Microtitanium Dioxide MT 600 B", by the company Degussa under the name "P 25", by the company Wackher under the name "Oxyde de titane transparent PW", by the company Myoshi Kasei under the name "UFTR", by the company Tomen under the name "ITS" and by the company Tioxide under the name "Tioveil AQ".

The uncoated zinc oxide nanopigments are, for example:

those sold under the name "Z-Cote" by the company Sunsmart;

those sold under the name "Nanox" by the company Elementis; and those sold under the name "Nanogard WCD 2025" by the company Nanophase Technologies.

The coated zinc oxide nanopigments are, for example:

those sold under the name "Zinc Oxide CS-5" by the company Toshibi (ZnO coated with polymethylhydrogenosiloxane);

those sold under the name "Nanogard Zinc Oxide FN" by the company Nanophase Technologies (as a 40% dispersion in Finsolv TN, $C_{12}$-$C_{15}$ alkyl benzoate);

those sold under the name "Daitopersion ZN-30" and "Daitopersion ZN-50" by the company Daito (dispersions in cyclopolymethylsiloxane/oxyethylenated polydimethylsiloxane, containing 30% or 50% of nanozinc oxides coated with silica and polymethylhydrogenosiloxane);

those sold under the name "NFD Ultrafine ZNO" by the company Daikin (ZnO coated with perfluoroalkyl phosphate and copolymer based on perfluoroalkylethyl as a dispersion in cyclopentasiloxane);

those sold under the name "SPD-Z1" by the company Shin-Etsu (ZnO coated with silicone-grafted acrylic polymer, dispersed in cyclodimethylsiloxane);

those sold under the name "Escalol Z100" by the company ISP (alumina-treated ZnO dispersed in an ethylhexyl methoxycinnamate/PVP-hexadecene/methicone copolymer mixture);

those sold under the name "Fuji ZNO-SMS-10" by the company Fuji Pigment (ZnO coated with silica and polymethylsilsesquioxane); and those sold under the name "Nanox Gel TN" by the company Elementis (ZnO dispersed at a concentration of 55% in $C_{12}$-$C_{15}$ alkyl benzoate with hydroxystearic acid polycondensate).

The uncoated cerium oxide nanopigments are sold under the name "Colloidal Cerium Oxide" by the company Rhone-Poulenc. The uncoated iron oxide nanopigments are sold, for example, by the company Arnaud under the names "Nanogard WCD 2002 (FE 45B)", "Nanogard Iron FE 45 BL AQ", "Nanogard FE 45R AQ" and "Nanogard WCD 2006 (FE 45R)" or by the company Mitsubishi under the name "TY-220". The coated iron oxide nanopigments are sold, for example, by the company Arnaud under the names "Nanogard WCD 2008 (FE 45B FN)", "Nanogard WCD 2009 (FE 45B 556)", "Nanogard FE 45 BL 345" and "Nanogard FE 45 BL" or by the company BASF under the name "Transparent Iron Oxide".

Mixtures of metal oxides may also be used, especially of titanium dioxide and of cerium dioxide, including the silica-coated equal-weight mixture of titanium dioxide and of cerium dioxide, sold by the company Ikeda under the name "Sunveil A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

The above lists are only examples and not limiting.

The compositions according to the instant disclosure may be prepared according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion.

The instant disclosure will be better understood from the examples that follow, all of which are intended for illustrative purposes only and are not meant to limit the scope of the instant disclosure in any way.

Example 1 (Inventive) and Comparative Example 2

The following sunscreen compositions were prepared and the SPF compared.

|  | Example 1 (Inventive) | Example 2 (Comparative) |
|---|---|---|
| DISODIUM EDTA | 0.1 | 0.1 |
| p-ANISIC ACID | 0.1 | 0.1 |
| ISOPROPYL LAUROYL SARCOSINATE | 4.75 | 4.75 |
| ISOTRIDECYL ISONONANOATE | 1.9 | 1.9 |
| STEARYL ALCOHOL | 0.18 | 0.18 |
| STYRENE/ACRYLATES COPOLYMER (SunSpheres ™) (Booster) | 3 | — |
| BIS-METHOXY PEG-13 PEG-438/PPG-110 SMDI COPOLYMER (Expert Gel) (Thermosensitive polymer) | 1 | — |
| PHENOXYETHANOL | 0.5 | 0.5 |
| DIMETHICONE | 1.45 | 1.45 |
| DIMETHICONE | 1.9 | 1.9 |
| DIMETHICONE (and) DIMETHICONOL | 0.95 | 0.95 |
| PEG-12 DIMETHICONE (Wetting Agent) | 0.25 | — |
| WATER | 61.49 | 65.74 |
| OXYBENZONE (BENZOPHENONE-3) (UV Filter) | 2.88 | 2.88 |
| OCTISALATE (ETHYLHEXYL SALICYLATE) (UV Filter) | 2.4 | 2.4 |
| OCTOCRYLENE (UV Filter) | 4.48 | 4.48 |
| HOMOSALATE (UV Filter) | 8 | 8 |
| AVOBENZONE (BUTYLMETHOXY-DIBENZOYLMETHANE) (UV Filter) | 2.24 | 2.24 |
| POLYSORBATE 61 | 0.45 | 0.45 |
| SODIUM STEAROYL GLUTAMATE | 0.45 | 0.45 |
| OCTYLDODECANOL (and) OCTYLDODECYL XYLOSIDE | 1.07 | 1.07 |
| GLYCERYL STEARATE | 0.36 | 0.36 |
| TOCOPHEROL | 0.1 | 0.1 |
| UV-A | 28.42 | 12.81 |
| SPF | 50 | 30 |

The data show that the sunscreen composition containing a booster, a thermosensitive polymer, and a filter (Example 1) exhibited a significant and unexpected improvement in UV-absorption and SPF compared to an equivalent composition without a booster, a thermosensitive polymer, and a filter (Comparative Example 2).

Comparative Examples 3-5 and Example 6 (Inventive)

The following sunscreen compositions were prepared and the SPF compared.

|  | Example 3 (Comparative) | Example 4 (Comparative) | Example 5 (Comparative) | Example 6 (Inventive) |
|---|---|---|---|---|
| DISODIUM EDTA | 0.1 | 0.1 | 0.1 | 0.1 |
| p-ANISIC ACID | 0.1 | 0.1 | 0.1 | 0.1 |

-continued

| | Example 3 (Comparative) | Example 4 (Comparative) | Example 5 (Comparative) | Example 6 (Inventive) |
|---|---|---|---|---|
| ISOPROPYL LAUROYL SARCOSINATE | 5 | 5 | 5 | 5 |
| ISOTRIDECYL ISONONANOATE | 2 | 2 | 2 | 2 |
| STEARYL ALCOHOL | 0.2 | 0.2 | 0.2 | 0.2 |
| STYRENE/ACRYLATES COPOLYMER (SunSpheres ™) (Booster) | — | — | — | 3 |
| BIS-METHOXY PEG-13 PEG-438/PPG-110 SMDI COPOLYMER (Expert Gel) (Themosensitive polymer) | — | 1 | — | 1 |
| PHENOXYETHANOL | 0.5 | 0.5 | 0.5 | 0.5 |
| DIMETHICONE | 1.5 | 1.5 | 1.5 | 1.5 |
| DIMETHICONE | 2 | 2 | 2 | 2 |
| DIMETHICONE (and) DIMETHICONOL | 1 | 1 | 1 | 1 |
| PEG-12 DIMETHICONE (Wetting Agent) | — | — | 0.25 | 0.25 |
| WATER | 64.6 | 63.6 | 64.35 | 60.35 |
| CAPRYLYL GLYCOL | 0.3 | 0.3 | 0.3 | 0.3 |
| OXYBENZONE (BENZOPHENONE-3) (UV Filter) | 2.88 | 2.88 | 2.88 | 2.88 |
| OCTISALATE (ETHYLHEXYL SALICYLATE) (UV Filter) | 2.4 | 2.4 | 2.4 | 2.4 |
| OCTOCRYLENE (UV Filter) | 4.48 | 4.48 | 4.48 | 4.48 |
| HOMOSALATE (UV Filter) | 8 | 8 | 8 | 8 |
| AVOBENZONE (BUTYLMETHOXY-DIBENZOYLMETHANE) (UV Filter) | 2.24 | 2.24 | 2.24 | 2.24 |
| POLYSORBATE 61 | 0.5 | 0.5 | 0.5 | 0.5 |
| SODIUM STEAROYL GLUTAMATE | 0.5 | 0.5 | 0.5 | 0.5 |
| OCTYLDODECANOL (and) OCTYLDODECYL XYLOSIDE | 1.2 | 1.2 | 1.2 | 1.2 |
| GLYCERYL STEARATE | 0.4 | 0.4 | 0.4 | 0.4 |
| TOCOPHEROL | 0.1 | 0.1 | 0.1 | 0.1 |
| SPF | 26 | 35 | 42 | 67 |

The data show that the sunscreen composition containing a booster, a thermosensitive polymer, and a filter (Example 6) exhibited a significant and unexpected improvement in UV-absorption and SPF compared to an equivalent composition without a booster, a thermosensitive polymer, and a filter (Comparative Example 3); an equivalent composition without a booster and a wetting agent (Comparative Example 4); and an equivalent composition without a booster and a thermosensitive polymer (Comparative Example 5).

It is claimed:
1. A sunscreen composition comprising:
   a. at least one UV filter;
   b. at least one booster;
   c. at least one thermosensitive polymer, wherein the at least one thermosensitive polymer is bis-methoxy PEG 13 PEG-438/PPG-110 SMDI copolymer; and
   d. at least one wetting agent.
2. The sunscreen composition according to claim 1 comprising about 1 to about 50 wt. % of the (a) at least one UV filter, based on the total weight of the sunscreen composition.
3. The sunscreen composition according to claim 1 comprising about 0.1 to about 25 wt. % of the (b) at least one booster, based on the total weight of the sunscreen composition.
4. The sunscreen composition according to claim 1 comprising about 0.1 to about 10 wt. % of the (c) at least one thermosensitive polymer, based on the total weight of the sunscreen composition.
5. The sunscreen composition according to claim 1 comprising about 0.01 to about 5 wt. % of the (d) at least one wetting agent, based on the total weight of the sunscreen composition.
6. The sunscreen composition according to claim 1, wherein the (b) booster is selected from the group consisting of styrene/acrylates copolymer, calcium aluminum borosilicate, sodium borosilicate particulates, calcium/sodium borosilicate hollow microspheres, and calcium/sodium borosilicate microspheres.
7. The sunscreen composition according to claim 6, wherein the (b) booster is styrene/acrylates copolymer.
8. The sunscreen composition according to claim 1, wherein the (d) at least one wetting agent is selected from the group consisting of a dimethicone copolyol compound.
9. The sunscreen composition of claim 8, wherein the (d) at least one wetting agent is PEG-12 dimethicone, which is a demithicone copolyol compound.
10. The sunscreen composition of claim 1, wherein the (a) at least one UV filter is a combination of UV filters comprising octocrylene, avobenzone, oxybenzone, octisalate, and homosalate.
11. The sunscreen composition of claim 10, wherein the UV filters are in a ratio relative to avobenzone is as follows:
    the ratio of octocrylene to avobenzone is 1.6:1.0 to 2.4:1.0;
    the ratio of oxybenzone to avobenzone 1.0:1.0 to 1.6:1.0;
    the ratio of octisalate to avobenzone is 0.8:1.0 to 1.3:1.0; and
    the ratio of homosalate to avobenzone is 2.8:1.0 to 4.3:1.
12. The sunscreen composition of claim 11, wherein the ratio of each UV filter relative to avobenzone is about: 2.0:1.0:1.3:1.1:3.6 (octocrylene:avobenzone:oxybenzone:octisalate:homosalate).
13. The sunscreen composition of claim 1, wherein the (a) at least one UV filter is a combination of UV filters comprising octocrylene, avobenzone, octisalate, and homosalate, and optionally oxybenzone.
14. The sunscreen composition of claim 13, wherein the UV filters are in a ratio relative to avobenzone is as follows:
    the ratio of octocrylene to avobenzone is 1.6:1.0 to 2.4:1.0,
    the ratio of oxybenzone to avobenzone 0.0:1.0 to 0.016:1.0,
    the ratio of octisalate to avobenzone is 1.3:1.0 to 2.0:1.0, and
    the ratio of homosalate to avobenzone is 2.3:1.0 to 3.6:1.
15. The sunscreen composition of claim 14, wherein the ratio of each UV filter relative to avobenzone is about: 2.0:1.0:0.0:1.7:3.0 (octocrylene:avobenzone:oxybenzone:octisalate:homosalate).
16. The sunscreen composition of claim 1, wherein the (a) at least one UV filter is a combination of UV filters comprising octocrylene, butyl methoxydibenzoylmethane, bis-ethylhexyloxyphenol methoxyphenyl triazine, ethylhexyl triazone, terephthalylidene dicamphor sulfonic acid, and drometrizole trisiloxane.
17. The sunscreen composition of claim 16, wherein the UV filters are in a ratio relative to butyl methoxydibenzoylmethane is as follows:

the ratio of octocrylene to butyl methoxydibenzoylmethane is 0.8:1.0 to 1.5:1.0;

the ratio of bis-ethylhexyloxyphenol methoxyphenyl triazine to butyl methoxydibenzoylmethane 0.3:1.0 to 0.8:1.0;

the ratio of ethylhexyl triazone to butyl methoxydibenzoylmethane is 0.3:1.0 to 1.0:1.0;

the ratio of terephthalylidene dicamphor sulfonic acid to butyl methoxydibenzoylmethane is 0.1:1.0 to 0.5:1.0; and the ratio of drometrizole trisiloxane to butyl methoxydibenzoylmethane is 0.3:1.0 to 1.0:1.0.

18. The sunscreen composition of claim 17, wherein the ratio of each UV filter relative to butyl methoxydibenzoylmethane is about: 1.2:1.0:0.5:0.6:0.4:0.6 (octocrylene:butyl methoxydibenzoylmethane:bis-ethylhexyloxyphenol methoxyphenyl triazine:ethylhexyl triazone:terephthalylidene dicamphor sulfonic acid:drometrizole trisiloxane).

19. The sunscreen composition of claim 1, wherein the (a) at least one UV filter is a combination of UV filters comprising octocrylene, butyl methoxydibenzoylmethane, ethylhexyl triazone, terephthalylidene dicamphor sulfonic acid, and drometrizole trisiloxane.

20. The sunscreen composition of claim 19, wherein the UV filters are in a ratio relative to butyl methoxydibenzoylmethane is as follows:

the ratio of octocrylene to butyl methoxydibenzoylmethane is 0.6:1.0 to 1.25:1.0;

the ratio of ethylhexyl triazone to butyl methoxydibenzoylmethane is 0.4:1.0 to 1.0:1.0;

the ratio of terephthalylidene dicamphor sulfonic acid to butyl methoxydibenzoylmethane is 0.3:1.0 to 0.7:1.0; and the ratio of drometrizole trisiloxane to butyl methoxydibenzoylmethane is 0.4:1.0 to 1.1:1.0.

21. The sunscreen composition of claim 20, wherein the ratio of each UV filter relative to butyl methoxydibenzoylmethane is about 1.0:1.0:0.7:0.5:0.7 (octocrylene:butyl methoxydibenzoylmethane:ethylhexyl triazone:terephthalylidene dicamphor sulfonic acid:drometrizole trisiloxane).

22. The sunscreen composition of claim 1, wherein the (a) at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane.

23. The sunscreen composition of claim 22, wherein the UV filters are in a ratio relative to butyl methoxydibenzoylmethane is as follows:

the ratio of octocrylene to butyl methoxydibenzoylmethane is 0.8:1.0 to 1.2:1.0;

the ratio of bis-ethylhexyloxyphenol methoxyphenyl triazine to butyl methoxydibenzoylmethane is 0.2:1.0 to 0.6:1.0;

the ratio of terephthalylidene dicamphor sulfonic acid to butyl methoxydibenzoylmethane is 0.0.25:1.0 to 0.75:1.0; and the ratio of drometrizole trisiloxane to butyl methoxydibenzoylmethane is 0.4:1.0 to 0.8:1.0.

24. The sunscreen composition of claim 23, wherein the ratio of each UV filter relative to butyl methoxydibenzoylmethane is about 1.0:1.0:0.4:0.4:0.6 (octocrylene:butyl methoxydibenzoylmethane:bis-ethylhexyloxyphenol methoxyphenyl triazine:terephthalylidene dicamphor sulfonic acid:drometrizole trisiloxane).

25. The sunscreen composition of claim 1, wherein the (a) at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane.

26. The sunscreen composition of claim 25, wherein the UV filters are in a ratio relative to butyl methoxydibenzoylmethane is as follows:

the ratio of octocrylene to butyl methoxydibenzoylmethane is 0.8:1.0 to 1.3:1.0;

the ratio of bis-ethylhexyloxyphenol methoxyphenyl triazine to butyl methoxydibenzoylmethane is 0.1:1.0 to 0.6:1.0;

the ratio of ethylhexyl triazone to butyl methoxydibenzoylmethane is 0.2:1.0 to 0.6:1.0; and the ratio of drometrizole trisiloxane to butyl methoxydibenzoylmethane is 0.3:1.0 to 0.7:1.0.

27. The sunscreen composition of claim 26, wherein the ratio of each UV filter relative to butyl methoxydibenzoylmethane is about 1.0:1.0:0.3:0.5:0.5 (octocrylene:butyl methoxydibenzoylmethane:bis-ethylhexyloxyphenol methoxyphenyl triazine:ethylhexyl triazone:drometrizole trisiloxane).

28. The sunscreen composition of claim 1, wherein the (a) at least one UV filter is a combination of UV filters comprising octocrylene, butyl methoxydibenzoylmethane, bis-ethylhexyloxyphenol methoxyphenyl triazine, terephthalylidene dicamphor sulfonic acid, and terephthalylidene dicampohor sulfonic acid.

29. The sunscreen composition of claim 28, wherein the UV filters are in a ratio relative to butyl methoxydibenzoylmethane is as follows:

the ratio of octocrylene to butyl methoxydibenzoylmethane is 0.8:1.0 to 1.6:1.0;

the ratio of bis-ethylhexyloxyphenol methoxyphenyl triazine to butyl methoxydibenzoylmethane is 0.2:1.0 to 0.6:1.0;

the ratio of ethylhexyl triazone to butyl methoxydibenzoylmethane is 0.3:1.0 to 0.6:1.0; and the ratio of terephthalylidene dicampohor sulfonic acid to butyl methoxydibenzoylmethane is 0.01:1.0 to 0.3:1.0.

30. The sunscreen composition of claim 29, wherein the ratio of each UV filter relative to butyl methoxydibenzoylmethane is about 1.2:1.0:0.3:0.5:0.1 (octocrylene:butyl methoxydibenzoylmethane:bis-ethylhexyloxyphenol methoxyphenyl triazine:ethylhexyl triazone:terephthalylidene dicampohor sulfonic acid).

31. The sunscreen composition according to claim 1 comprising:

a. about 20 wt. % of at least one UV filter;

b. about 3 wt. % of at least one booster, wherein the at least one booster is styrene/acrylates copolymer;

c. about 1.0 wt. % of at least one thermosensitive polymer, wherein the at least one thermosensitive polymer is bis-methoxy PEG 13 PEG-438/PPG-110 SMDI copolymer; and d. about 0.25 wt. % of at least one wetting agent, wherein the at least one wetting agent is PEG-12 dimethicone.

32. A method of protecting a keratinous substrate from ultraviolet radiation comprising applying a sunscreen composition according to claim 1 to the keratinous substrate.

33. A method of absorbing ultraviolet light comprising applying a sunscreen composition according to claim 1 to a keratinous substrate and subjecting the keratinous substrate to ultraviolet light.

* * * * *